United States Patent [19]

Lassen et al.

[11] Patent Number: 4,804,380
[45] Date of Patent: Feb. 14, 1989

[54] ANATOMICALLY SHAPED, SELF-ALIGNING, SANITARY PROTECTION DEVICE

[75] Inventors: Frederich O. Lassen; Anna M. Cesco-Cancian; Dawn M. Huffman, all of Neenah, Wis.

[73] Assignee: Kimberly-Clark Corporation, Neenah, Wis.

[21] Appl. No.: 82,883

[22] Filed: Aug. 6, 1987

[51] Int. Cl.⁴ .............................................. A61F 13/16
[52] U.S. Cl. .................................. 604/385.1; 604/378; 604/393
[58] Field of Search ............... 604/385, 378, 393, 358, 604/367, 368, 369, 370, 374

[56] References Cited

U.S. PATENT DOCUMENTS

| | | | |
|---|---|---|---|
| 1,857,854 | 5/1932 | Glomstead | 604/375 |
| 2,064,431 | 12/1936 | Jurgensen | 128/290 |
| 2,331,355 | 10/1943 | Strongson | 604/385 |
| 2,964,039 | 12/1960 | Johnson, Jr. et al. | 128/290 |
| 3,121,427 | 2/1964 | Mosier | 604/368 |
| 3,575,174 | 4/1971 | Mogor | 128/290 |
| 4,340,058 | 7/1982 | Pierce et al. | 604/385 |
| 4,490,147 | 12/1984 | Pierce et al. | 604/378 |
| 4,631,062 | 12/1986 | Lassen et al. | 604/385 |
| 4,673,403 | 6/1987 | Lassen et al. | 604/385 |

Primary Examiner—William R. Dixon, Jr.
Assistant Examiner—Ann M. Knab
Attorney, Agent, or Firm—Paul A. Leipold; Thomas J. Connelly

[57] ABSTRACT

The invention is generally accomplished by forming a three-dimensionally shaped, externally worn feminine protection device which has been mechanically shaped by folding, molding or other forming techniques in such a way that it has a raised portion located within the back one-half to two-thirds of the device that functions to cause the pad to readily fit to and generally align itself within the inverted V-shaped regions of the woman's lower abdominal region, vulva, perineum and the anterior portion between the buttocks. The forward portion of the device of the invention generally is flattened in use to cover externally the area of the pubic mons and the area exterior of the clitoris. The back portion of the device is formed in a peak like shape which readily adjusts to and molds to the inverted V-shape of the rear portion of the labia, the perineum and the forward portion of the area between the buttocks.

21 Claims, 11 Drawing Sheets

ANATOMICALLY SHAPED, SELF-ALIGNING, SANITARY PROTECTION DEVICE

TECHNICAL FIELD

The present invention relates generally to the field of devices for absorbing bodily exudate, particularly sanitary napkins for personal feminine care. The pads of the invention also find use in absorption of urine as a consequence of minor incontinence.

BACKGROUND ART

There have been a variety of devices or applicances cofigured for catamenial devices. Generally there have been offered two basic kinds of feminine protection device. These are sanitary napkins or pads that have been developed for external wear, and tampons that have been developed for residence within the vaginal cavity and interruption of menstrual flow therefrom. Each has offered distinct advantages. Hybrid devices attempted to merge the structural features of both within a single type of device have also been proposed.

There has been proposed in U.S. Pat. No. 4,631,062—F. O. Lassen et al. a labial pad that is particularly advantageous in that it is a discreet, comfortable, and highly effective pad. However, while this pad has been particularly successful in functioning as a catamenial device when properly placed, its small size and unique design has made difficult the education of the wearer as to proper placement.

It has been proposed in U.S. Pat. No. 4,673,403 to improve the placement of the catamenial device of U.S. Pat. No. 4,631,062—Lassen et al. by providing an indicator on the bodyside of the pad to aid in proper placement of the pad onto the body of the wearer. While the above pads of Lassen et al. have performed well they have the difficulty that they are not well accepted by the consumer as they are so small that the consumers do not find them believable as to their effectiveness. Further, for best performance they need to be placed on the body first and then held in place by an undergarment. This is contrary to the common practice of consumers in which pads are fastened to their undergarments prior to placement on the body.

Therefore, there is a need for a pad that will have the performance benefits of the above Lassen et al. pads with improved flexibility in the method of placement on the body and with a larger size that is more believable to the consumer.

DISCLOSURE OF THE INVENTION

The object of this invention is to overcome disadvantages of prior catamenial devices.

A further object is to form a feminine pad that is self-aligning to maintain correct placement of the pad on the body.

A further object of the invention is to provide a pad that resists bunching and twisting when worn.

A further additional object of the invention is to create a feminine pad that is discreet and comfortable when worn.

These and other objects of the invention are generally accomplished by forming a three-dimensionally shaped, externally worn feminine protection device which has been mechanically shaped by folding, molding or other forming techniques in such a way that it has a raised portion located within the back one-half to two-thirds of the device that functions to cause the pad to readily fit to and generally align itself within the inverted V-shaped regions of the woman's lower abdominal region, vulva, perineum and the anterior portion between the buttocks. The forward portion of the device of the invention generally is flattened in use to cover externally the area of the pubic mons and the area exterior of the clitoris. The back portion of the device is formed in a peak like shape which readily adjusts to and molds to the inverted V-shape of the rear portion of the labia, the perineum and the forward portion of the area between the buttocks.

MODES FOR CARRYING OUT THE INVENTION

Traditional feminine hygiene protection generally comes from two sources, i.e., either sanitary napkins or tampons. Each has certain disadvantages. Sanitary napkins are designed to be worn externally and as such as susceptible to failure because of side crunching and shifting. Most pads are also flat and very bulky and because of their flat geometry, do not readily mold to the contours of female anatomy and therefore tend to leak prematurely over the sides. In fact, they generally rely on the motions and the pressures of the user's body and garments to cause them to adapt to the body's curvatures. Because of this, the pads do not interface and mold well to the body and the usual walking motions tend to cause the pad's side edge to insert into the folds of the buttock rather then to be aligned equally along the body's center line. During use, the end of conventional pads tends to remain unused. Also, the conventional pads are generally long and bulky in the rear, and therefore protrude so as to be visible under certain type of tight fitting clothing. Because of these various problems, fluids tend to build up on the surface and generally show side rather than end failure.

Tampons, on the other hand, are much smaller than pads since they are designed to be worn within the vaginal cavity. Tampons, while not having the external bulk of the pads, have certain disadvantages. Depending upon the tampon, there are insertion difficulties, internal discomfort during its residence, removal difficulties, as well as psychological and moral dislikes by some women for vaginal insertion.

Interlabial pads which, with varying degrees of success combine the best features of both tampons and pads while avoiding the disadvantages of each, have been developed. Historically, "large" means protection to the woman and conventional "small" pads are considered to be useful only for light flow. Therefore, because of the relative small size, the labial products which are the functional equivalent of the "large" pads suffer from size related user insecurity and resistance to the learning required for their proper placement.

The instant invention, because of its unique shape and construction, overcomes many of the disadvantages of the above menstrual devices. Tampons are generally considered to be more comfortable, convenient and especially to be less "wet and messy" than pads because of being worn internally. The external nature of the instant invention overcomes the insertion stigmas related to tampons. Also, because of its shape, the instant invention is more comfortable and easier to carry and place than the conventional external products and approaches the comfort and convenience of tampons. The invention's configuration which readily accommodates the female anatomy, allows fluid interception in the vulva at the exterior juncture of labia, and delivers a self-aligning characteristic which overcomes much of the placement, "wet and messy", and other comfort problems of conventional external products. The relative larger size of this invention overcomes the "smallness" related insecurity and positioning problems of some labial products. While not molding into the vestibule as do the labial products, it does fit much better to the external curvature of the vulva and labia than the conventional flat napkins and pads. It also exhibits fluid interception, top staining and surface dryness properties much closer to that of the labial products than the conventional pads of similar composition. In fact, this invention delivers, visually, perceptions of protection and security which are superior to both the conventionally sized flat products and the much smaller labial products.

The invention provides a pad constructed and shaped in such a way as to allow the front portion of it to fit over and conform to the flattened forward portion of the female genitalia and lower abdomen while the rear portion of the pads aligns with and fits comfortably into the cross-like regions of the buttock and perineum to such an extent as to allow a surprisingly efficient external interception of exudate while at the same time giving the user the psychological assurance against leakage generally associated with the larger flat conventional napkin and pads. The absorbent pad of the invention provides better alignment with the female anatomy and closer contact with the vulva than is possible with current flat pads. The improved alignment of the pad minimizes bunching and twisting while providing efficient exudate collection. The pad further is comfortable and discreet in use as it is closely shaped to the anatomy. The effectiveness of the instant pad is surprising as previously it was considered that a pad folded in use into an inverted V would be subject to leakage. The pad of the invention having generally parallel longitudinal sides and rounded ends is low in cost to form and does not require the utilization of exotic materials or forming techniques. These and other advantages of the invention will be apparent from the following detailed description.

FIGS. 1 through 5 are top, side, bottom and the two end views of a pad 10 in accordance with the invention. The pad has a top 12 and ends 14 and 16. The pad is provided with a peel strip 18 on the back of forward area 30 covering two lines of adhesive 20 and 22. The pad has a border 24 where the cover 26 is bonded to the backing sheet 28. The portion of the pad forming the forward end 14 in use is generally flat as best shown by area 30 in FIG. 2. The rearward portion 32 is provided with a peak 34. The center area of peak 34 is held by adhesive dots 36, 38 and 40 on the back 13 of the pad 10. The peaked portion 32 forms a gradual rise from its beginning at area 42 to end 44. In use the pad 10 is placed such that the flattened forward area 30 extends generally over the forward portion of the female anatomy in the mons pubis and the forward portion of the labia. The raised portion 32 extending from 42 to 44 generally begins in the pudendal cleft rearward portion of the labia adjacent the vestibule and extends to the perineum and buttocks. The exact placement of the raised portion will vary depending on whether the pad is long enough to extend to the buttocks area.

Figure 1:
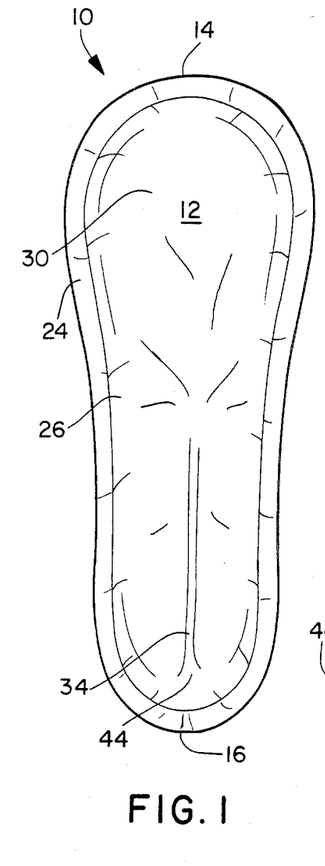
FIG. 1 is a top view of the pad of the invention.
Figures 2, 3:
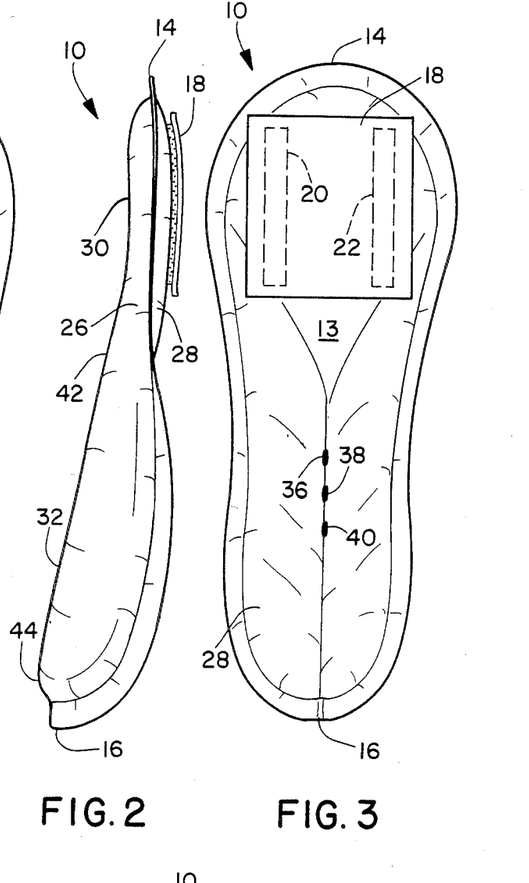
FIG. 2 is a side view of the pad of FIG. 1.
FIG. 3 is a bottom view of the pad of FIG. 1.
Figures 4, 5:
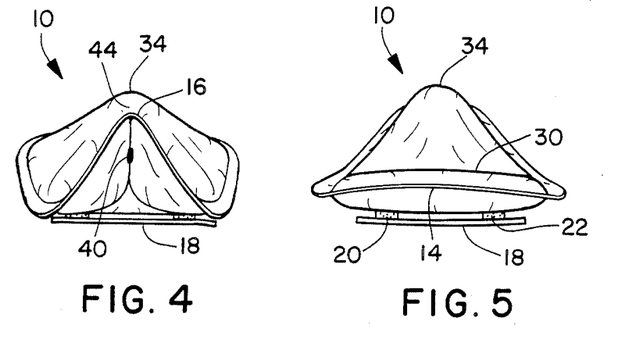
FIGS. 4 and 5 are the end views of the pad of FIG. 1.
Figure 6:
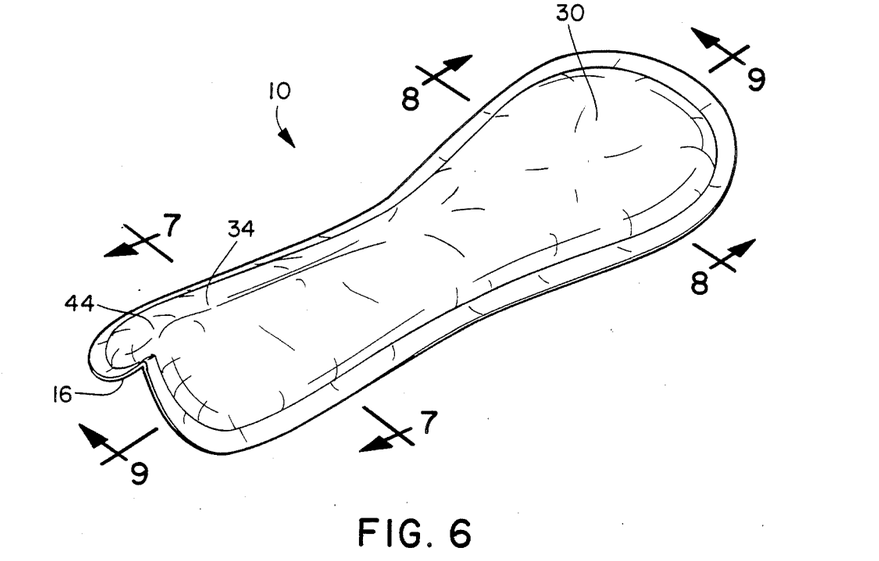
FIG. 6 is a perspective view of the pad of FIG. 1.
Figure 7:
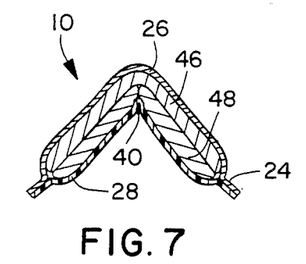
FIG. 7 is a cross-sectional view of the pad of FIG. 6 on line 7—7.
Figure 8:
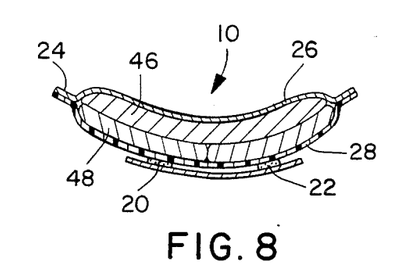
FIG. 8 is a cross-sectional view of the pad of FIG. 6 on line 8—8.
Figure 9:
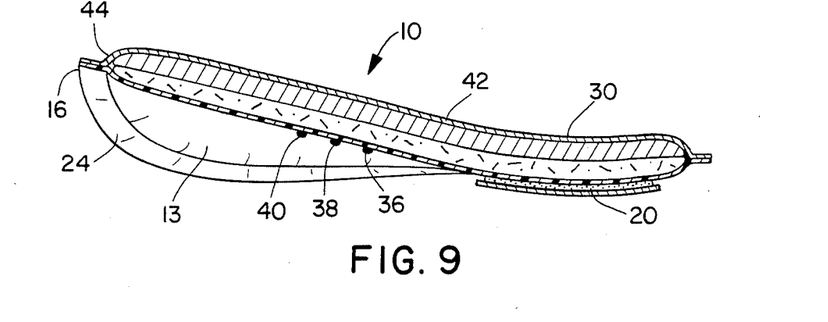
FIG. 9 is a cross-sectional view of the pad of FIG. 6 on cross-sectional line 9—9.

FIGS. 6 through 9 illustrate in perspective view FIG. 6 and in cross-sectional views of FIGS. 7-9 pad 10 as it would be configured during use. The forward end 30 would be concave to mold to the pubic mons and the lower abdomen. The rearward portion 16 would be peaked for placement between the legs at the perineum and between the buttocks. As illustrated in the cross-sectional views the absorbent is comprised of two sections 46 and 48. Section 46 is primarily a transfer layer that transfers fluids away from the bodyside cover member 26.

Figure 10:
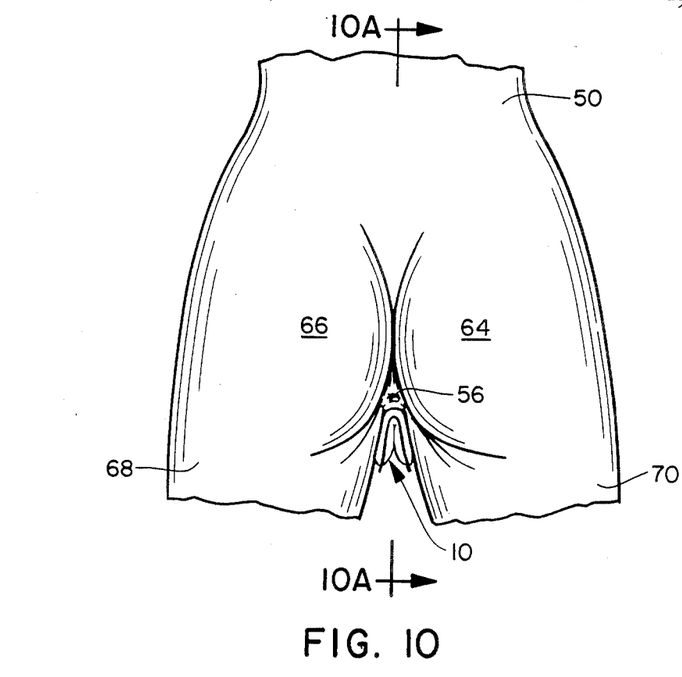
FIG. 10 is a back view of a body with a pad of the invention in place.
Figure 10A:
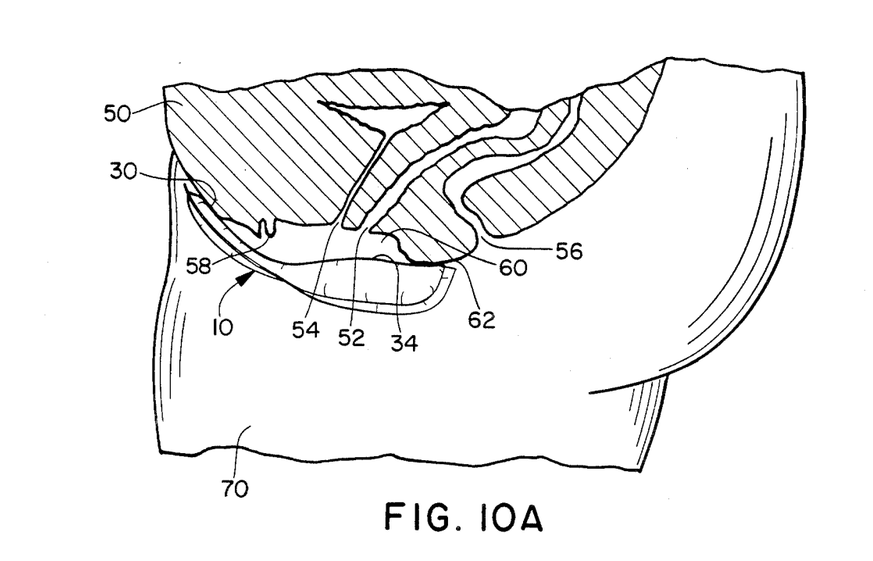
FIG. 10A is a cross-sectional view of FIG. 10 on cross-sectional line 10A of FIG. 10.
Figures 11, 12, 13, 14, 15:
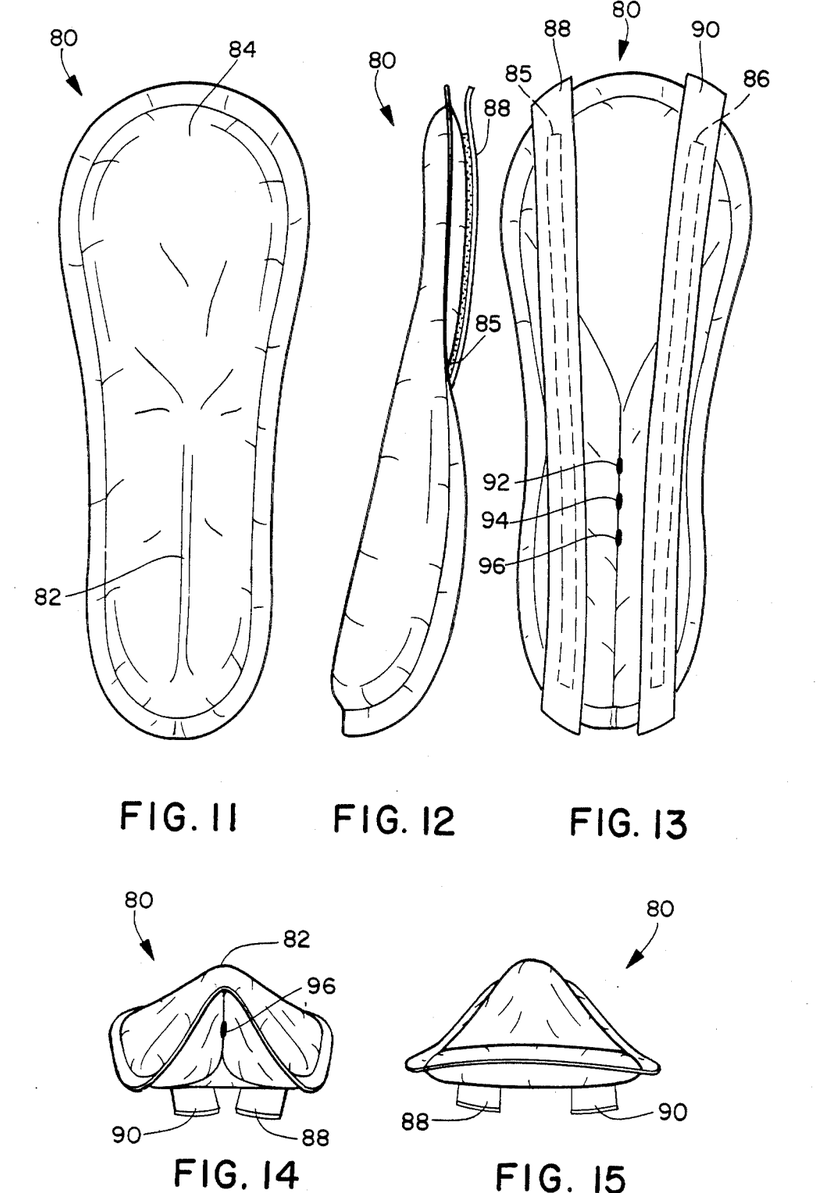
FIGS. 11, 12, 13, 14, and 15 are top, side, bottom and end views of an alternate pad of the invention.

FIG. 10 is a rear view of a woman with pad 10 in place. The view is from the rear with buttocks 64 and 66 and legs 68 and 70. FIG. 10A, on cross-sectional line 10A—10A of FIG. 10, is a view of a pad of the invention placed as in use. The pad 10 is placed onto the female body 50. The body has vaginal opening 52, urethral opening 54 and rectum 56. The flattened or concave portion of the pad 30 is placed against the pubic area. The pad when in use is at a distance from the clitoris 58. The raised portion of the pad 34 is generally exterior of the labia. However, in the area of the vestibule 60 it may extend somewhat between the labia. The pad 10 ends in the perineal area 62 and does not quite extend to the rectum 56. However, longer pads of the invention may extend further and be comfortable as the raised section 34 fits comfortably between the buttocks.

FIGS. 11 through 14 are views of an alternate embodiment of the invention. Pad 80 has raised portion 82 and flattened portion 84. The pad is provided with extended adhesive portions 85 and 86 that are covered by peel strips 88 and 90. The central area of the peaked portion 82 is held in place by adhesive areas 92, 94 and 96 for secure fastening to the undergarment of the wearer.

Figure 16:
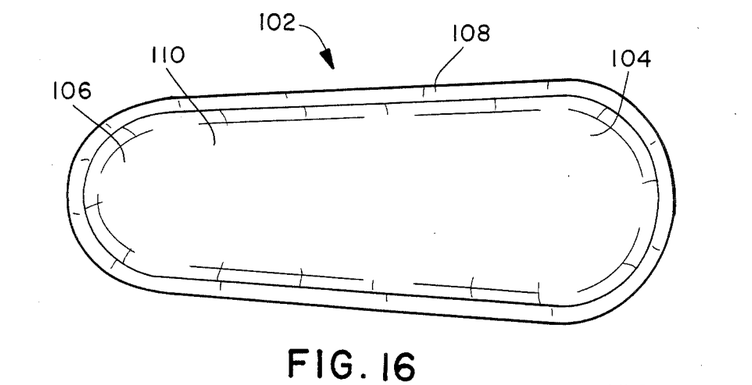
FIG. 16 is a top view of an alternate pad of the invention.
Figure 17:
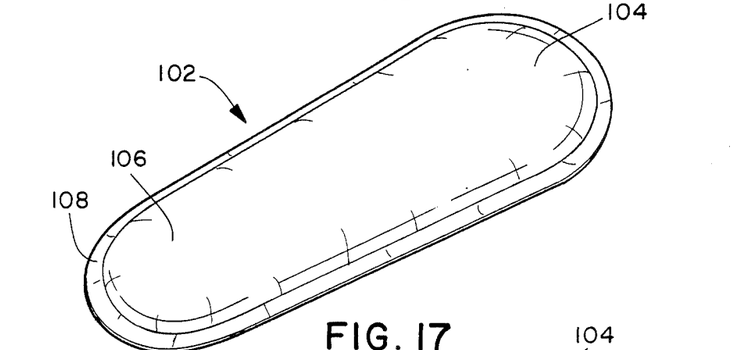
FIG. 17 is a perspective view of the pad of FIG. 16.
Figure 18:
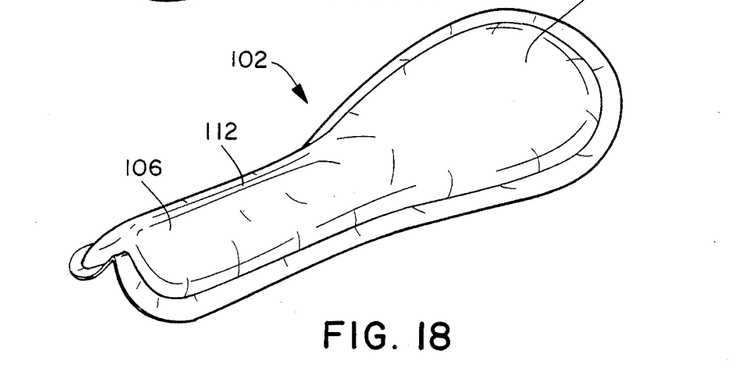
FIG. 18 is the pad of FIG. 16 shaped as in use.

FIGS. 16, 17 and 18 illustrate a tapered pad 102 that has a wider portion 104 in the front and tapers to a narrower rear portion 106. The pad has an edge 108 where the bodyside liner 110 and the backing layer, not shown, are joined. As illustrated in FIG. 18 when the pad is shaped to the desired shape for pads of the invention the front portion 104 forms a flattened or concave portion to fit over the front pubic area and labia of the wearer while the rear portion 106 forms a peak 112 for placement in the crease of the perineal and buttock area.

Figure 19:
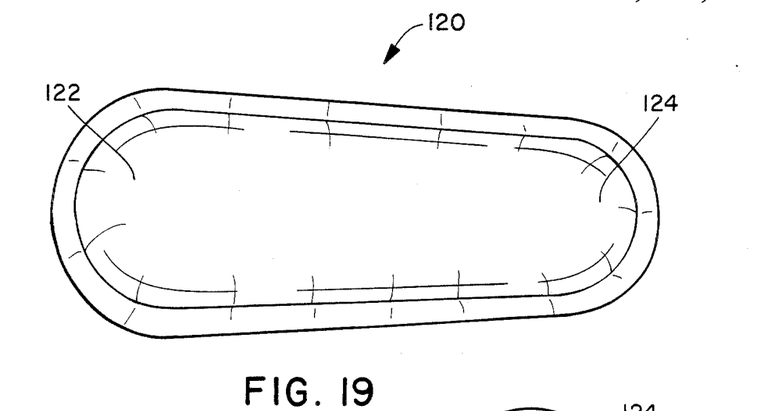
FIG. 19 is a top view of an alternate pad of the invention.
Figure 20:
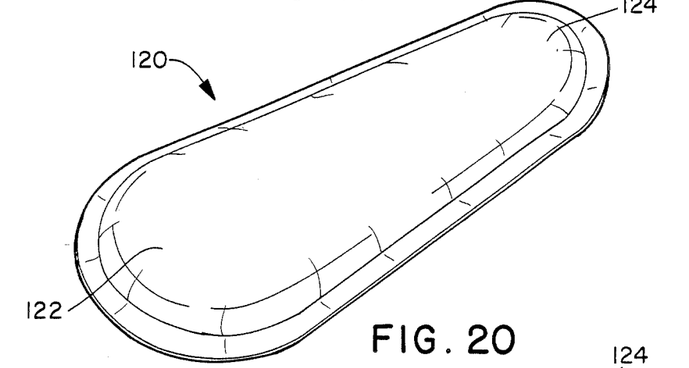
FIG. 20 is a perspective view of the pad of FIG. 19 prior to folding.
Figure 21:
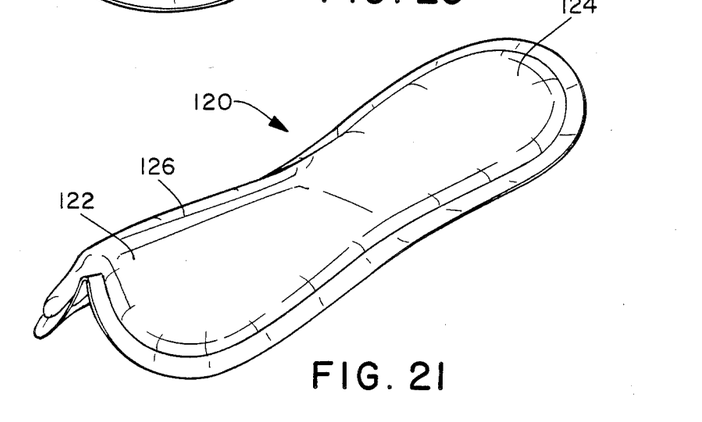
FIG. 21 is the pad of FIG. 20 folded as in use.

FIGS. 19 through 21 illustrate a pad 120 that is illustrated in the top view prior to folding. FIG. 19 has a larger rear portion 122 than front portion 124. The perspective views of pad 120 in FIGS. 20 before folding and 21 after folding to shape illustrate that the pad after being folded to shape has a front portion 124 and a rear portion 122 having a raised peak 126. The raised peak 126 when formed from the wider portion of the pad causes cupping in front area 124.

Figure 22:
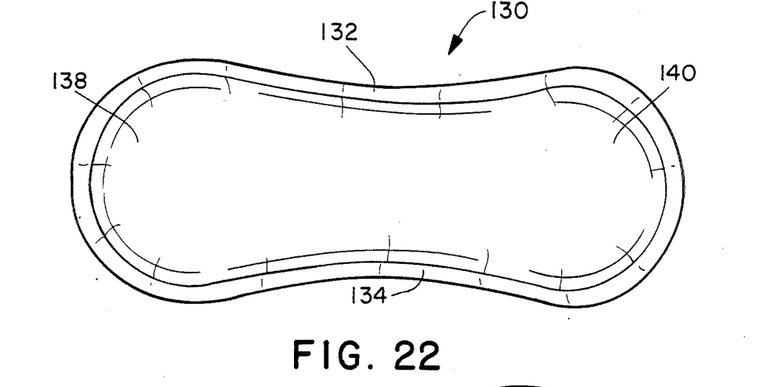
FIGS. 22, 23 and 24 are top, perspective, and folded views of an hourglass shaped pad of the invention.
Figures 23, 24:
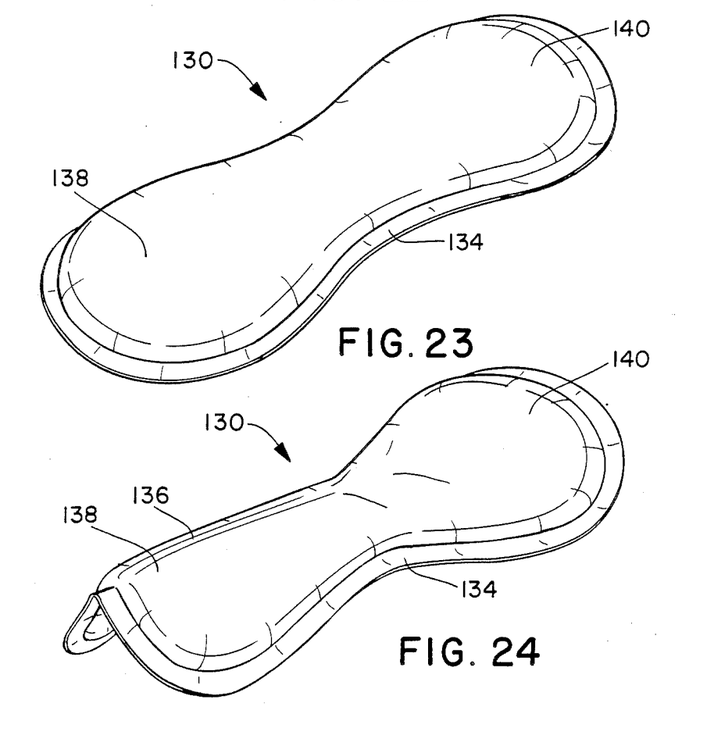
Figure 25:
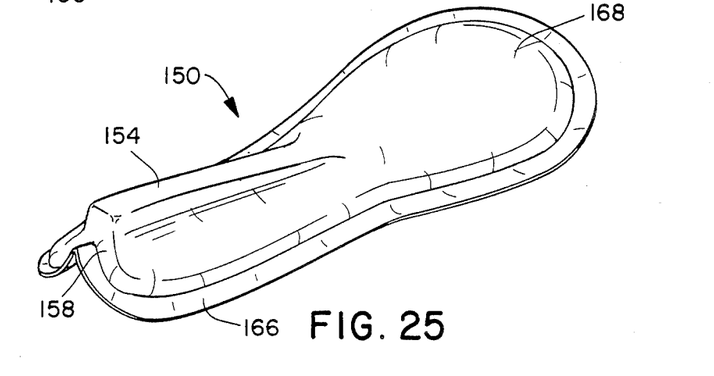
FIG. 25 is a perspective view of an alternate embodiment pad of the invention.
Figure 26:
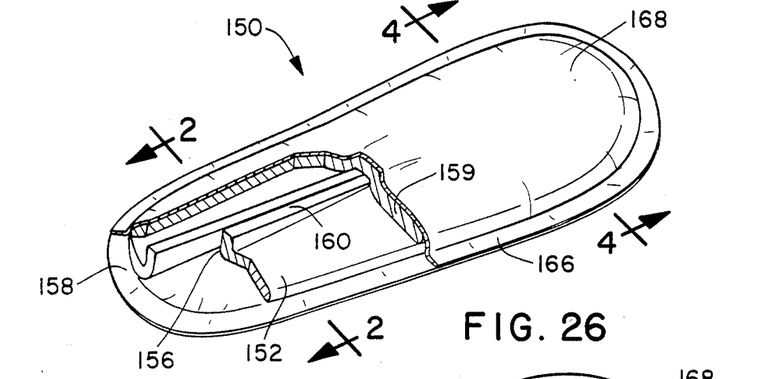
FIG. 26 is a partial cutaway view of the pad of FIG. 25.
Figure 27:
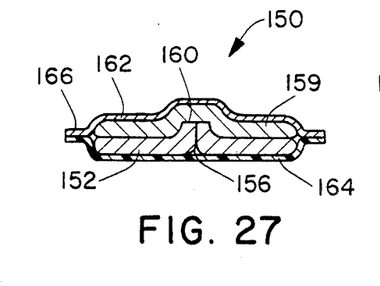
FIG. 27 is a cross-sectional view of the pad of FIG. 26 on cross-sectional line 2—2.
Figure 28:
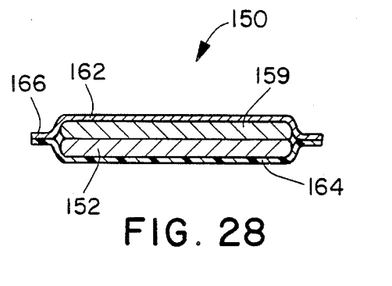
FIG. 28 is a cross-sectional view of the pad of FIG. 26 on cross-sectional line 4—4.

The embodiment of FIGS. 22, 23 and 24 is a pad 130 having an hourglass shape with narrower portions on longitudinal edges 132 and 134. The pad after folding has the raised peak area 136 at the rear portion 138. The front portion 140 remains generally flat and will mold to the pubic and forward labia area of the wearer.

Illustrated in FIGS. 25, 26, 27 and 28 is a pad 150 that is provided with an absorbent 152 that is thicker in the peaked area 154. The absorbent 152 is slit and then the areas of the slit turned up at 156 to form a raised central portion in the rear portion 158 of the pad 150. This thicker portion 156 is then covered by the soft transfer layer 159 that serves to transfer fluid to the absorbent 152. Orientation of the fibers at the raised portion 160 aids in rapid absorption in the area of the peak 154. The bodyside cover 162 is sealed to the garment or backing layer 164 at side seal 166. The front portion 168 is generally flat for molding to the forward pubic area of the wearer.

Figures 29, 30, 31:
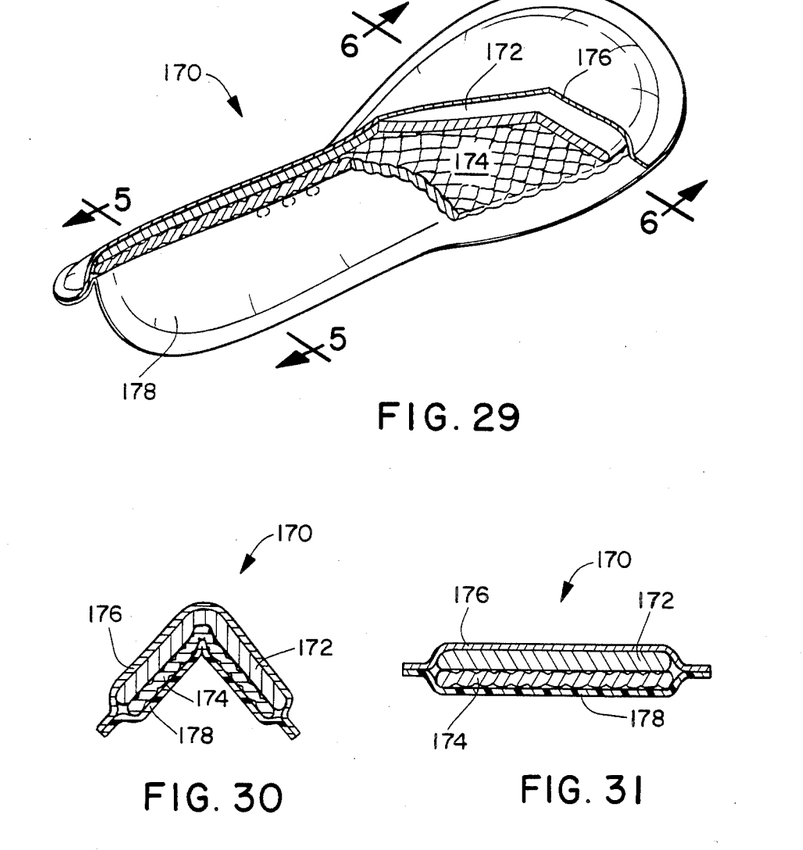
FIG. 29 is a partial cutaway view of an alternate pad of the invention.
FIG. 30 is a cross-sectional view of the pad of FIG. 29 on cross-sectional line 5—5.
FIG. 31 is a cross-sectional view of the pad of FIG. 29 on cross-sectional line 6—6.
Figure 32:
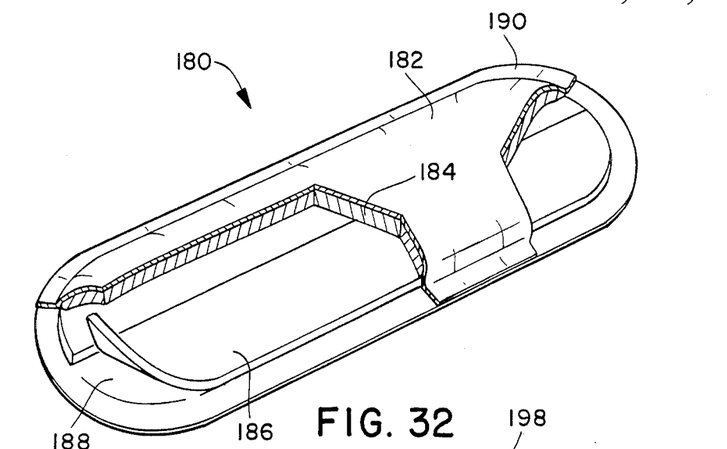
FIG. 32 is a partial cutaway view of a pad of the invention.
Figure 33:
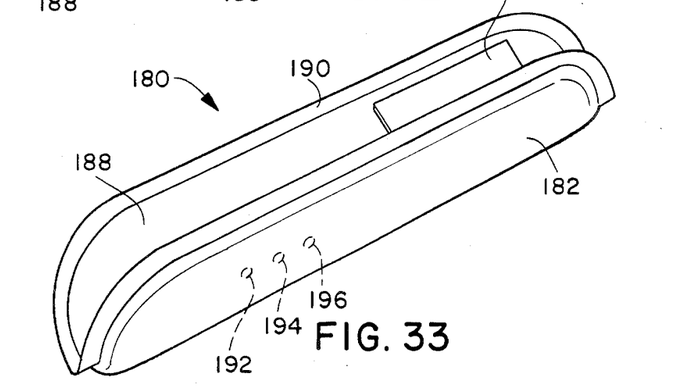
FIG. 33 is a perspective view of the pad of FIG. 32 folded.
Figure 34:
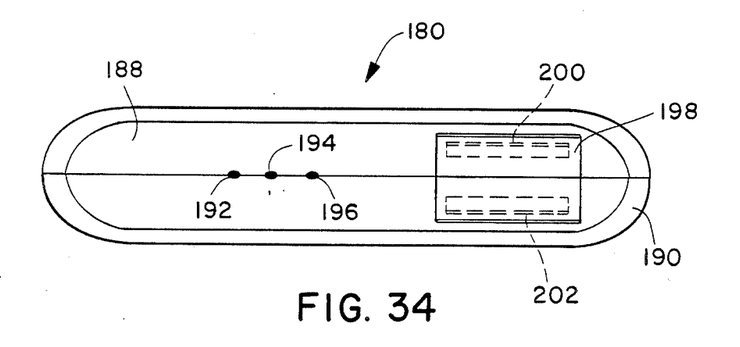
FIG. 34 is a bottom view of the pad of FIG. 33 folded.

Illustrated in FIGS. 29, 30 and 31 is an embodiment of the pad 170 with a preferred two-layer absorbent structure. The structure is low in cost and effective as it contains a bodyside layer 172 of low density wood pulp and a lower layer 174 of densified fluff. The liquid permeable bodyside liner 176 overlays the low density layer 172 while the impermeable backing layer 178 is beneath the densified layer. This structure gives good transfer of fluids through the upper less dense layer 172 for absorption into the densified layer 174. By transmission of fluid to the lower layer 174 the cover 176 remains drier.

Figure 35:
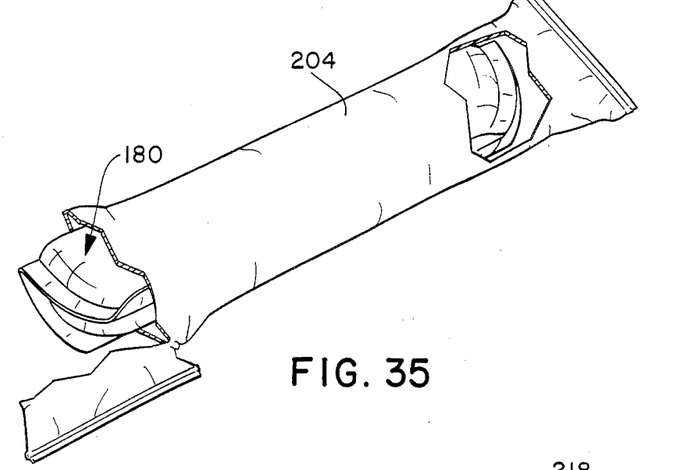
FIG. 35 is a partial cutaway view of the pad of FIG. 33 placed into a package.

FIGS. 32 through 35 illustrate a pad 180 of the invention that is convenient to form and package. The pad 180 is provided with a permeable cover 182. The absorbent is formed of a less dense upper transfer layer 184 and a more dense lower absorbent layer 186. Backing member 188 is formed of an impermeable polymer sheet. The cover 182 and backing sheet 188 are sealed together by heat or adhesive at edge 190. The pad that is viewed in FIG. 33 in perspective and in FIG. 34 from the back is folded and the center of the fold held in place at one end by glued areas 192, 194 and 196. The pad 180 is provided with a peel strip 198 and two lines of adhesive 200 and 202 on the forward end of the pad. As illustrated in FIG. 35 the pad 180 when folded may be easily wrapped in a small package 204.

Figure 36:
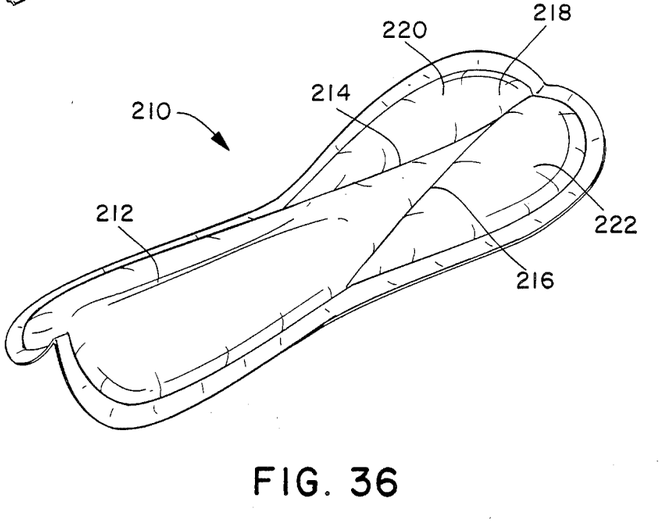
FIG. 36 is a view of an alternate pad of the invention.

FIG. 36 illustrates an alternate embodiment of the invention in which pad 210 has a raised rearward portion 212. The pad is provided with grooves 214 and 216 where the raised portion 212 descends into the flattened front portion 218. The pad 210 if folded on line 212 to form the raised portion and folded on lines 214 and 216 such that the edge portions 220 and 222 face each other forms a compact folded product that when unwrapped has generally the shape required for use. The fold lines at the grooves 214 and 216 extend along the edges of where the peaked portion 212 rises from the flattened front portion 218 and the compressed grooves 214 and 216 come together in a V at the front of the pad. In contrast the product 180 requires more shaping by the user prior to application in order to form the flattened front portion and the peaked rearward extending portion.

The pads of the invention may be provided with any absorbent that is capable of absorbing human exudate. Suitable for the invention are polyester fibers, rayon fibers, cotton fibers, and mixtures of these fibers with or without surfactant treatment. Preferred fibers for the invention are wood fluff fibers and coform nonwoven webs. Coform is an airformed blend of meltblown polypropylene microfibers and staple wood fibers. These materials are preferred as wood fluff is low in cost. Coform has integrity when wet and also is low in cost. In a preferred form of the invention the absorbent may be formed of more than one layer. The layer of absorbent toward the bodyside would be formed with a lower density such that it would serve as a transfer layer to transfer fluid to the absorbent layer adjacent the backing member that would be of greater density. The absorbent of greater density would preferentially absorb fluids from the surface layer absorbent of lower density. Therefore the layer underneath the permeable cover would be drier and the cover would feel drier to the wearer.

The bodyside cover or bodyside liner may be any permeable material that will pass human exudate to the absorbent. Typical of such materials are tissue, perforated films, and woven gauze material. Polypropylene spunbonded and polypropylene and rayon blends in thermobonded nonwovens are suitable for the products of the invention. A preferred material is a polyester thermobonded nonwoven of staple fibers having a basis weight of about 10 to about 60 gsm, that may or may not be treated with a surfactant as these materials provide a soft and dry feel to the pad. A typical cover is the spunlaced polyester sold under the trade name "Sontara" by E. I. DuPont Company that is comprised of a polyester fiber having a basis weight of about 34 grams per meter.

The liquid impermeable backing member may be any material that will block the flow of human exudate from the bodyside to the garment of the wearer. Typical of such materials are polymer films of polyethylene and polypropylene. Further, the polymer films may be combined with a nonwoven material such as spunbonded polypropylene to create a clothlike outer cover. It is also possible that vapor permeable but liquid impermeable backing members could be utilized. In another embodiment of the invention the impermeable backing material used is a molded foam material that provides correct pad shape without shaping by the user.

The pad has been described with two layers of absorbent having different densities as the preferred embodiment. However, the pad also could be formed with a single absorbent layer. It is also possible that a transfer layer having little absorption ability could be located immediately below the bodyside cover. Typical of such material is a fibrous material such as blends of polyester and rayon that have minimum fluid retaining character. Such material will rapidly transfer fluid from the cover to the absorbent but will not absorb a significant amount of the fluid. Other transfer layers may be airformed or carded webs of polyester, rayon or polypropylene.

The peak portion of the pad may be completely formed prior to delivery of the pad to the consumer. Alternatively, the peak may only be present in an embryonic or precursor state that allows the user to form the peak in its correct state by folding the pad in the preferential fold that the precursor allows. Such precursor could be a longitudinally split absorbent in the rear portion of the pad or, as illustrated, a series of adhesive dots forming a tuck in the pad. Depending on the nature and composition of the absorbent and backing material, the embryonic peak may be formed in many ways, including heat setting or thermo plastic containing absorbents or thermo plastic backing members. Other approaches will occur to the skilled artisan for achieving the goal of providing the peak precursor or embryonic fold line, which in turn assists the user in forming the desired peak profile or inverted V of the pad in which the bodysides of the pad, as well as the side of the pad away from the body, form an inverted V with the sides sloping away from the peak on the bodyside and backside of the pad.

The adhesive that forms a tuck in the backing member to provide a beginning point for the peak when the pad is formed may be located in any suitable area. The area where the tucks are located is generally in the midportion of the rearward half of the pad. The tuck adhesive is located generally so as to form a folded area of between about ⅛ and ⅜ inches in the backing material. This tucked area provides an embryonic fold to aid in molding of the pad to form the peaked area that conforms to the rear portion of the labia, the perineum and buttocks. The adhesive used may be any suitable adhesive product, including two-sided tape and the common hotmelt construction adhesives utilized in feminine care and diaper products. The tuck or peak precursor area also may be formed by thermal bonding.

As described above the pads of the invention generally are provided with a pressure-sensitive garment attachment adhesive on at least a portion of the liquid impermeable backing member. The pressure-sensitive adhesive and peel strip suitably is any of those well known in the feminine care art.

The pads of the invention may be formed in any size suitable for absorption of human exudate. Generally the pads have a length of between about 7 and about 12 inches. The preferred length is generally between about 7 and 8 inches as this length is discreet, effective and easily placed in the correct position. The width generally is equal to between about 2 and about 4 inches. The preferred width is about 2.5 inches for comfort and effectiveness in absorption of menstrual fluids. Generally pads designed for incontinence use for women with mild urinary or fecal incontinence are longer and thicker particularly in the rear than pads designed for menstrual use. The length and height of the ridge or peak in the rearward portion of the pad of the invention is determined by the sharpness of the fold, the arrangement of the absorbent and the location and length of the adhesive that holds the fold in place. The fold is useful for aligning the pad with the body's contours as the device is being positioned on the body of the user. By using adhesive of the pressure-sensitive or cohesive type for joining the sides of the crease or fold the user may selectively partially break the adhesives section to adjust the height to the peak for best comfort and protection for a particular body size. The longitudinal folded nature of the pad allows the invention to be packaged in a longitudinally folded configuration and after removal from the package the invention's front flat portion and rear peaked section may be adjusted by the individual in placement of the pad on the body. The cupped or concave front portion of the pad may be achieved by inverting the peak of the folded version near the pad's front.

While the invention has been discussed with particular reference to the preferred catamenial pads, it is also desirable for pad devices for incontinence protection or other types of vaginal discharge. Further, the pad may be formed in various sizes and shapes to best conform to the body of the users. Further, while the pad has been described as useful primarily for women large size pads with the concave front and peaked rear also would be suitable for male incontinence use. These and other variations of the invention are intended to be included by the invention which is only to be limited by the scope of the claims attached hereto.

We claim:

1. A pad for absorption of human exudate comprising an impermeable outer cover, a liquid permeable bodyside web and an absorbent therebetween, said pad comprising a flattened front portion for positioning exterior of the clitoris and pubic mons and a rearward portion having an upraised peak for positioning in alignment with the creases of the perineum, buttocks and rearward portion of the pudendal cleft wherein the rearward portion of said pad is folded generally at its longitudinal center to form said peak and has a length greater than about 7 inches.

2. The pad of claim 1 wherein said peak of said rearward portion is generally continuous and said peak rises gradually from said flattened portion.

3. The pad of claim 1 wherein said pad is folded generally at its longitudinal center to form said peak.

4. The pad of claim 2 wherein the rear about one-half to two-thirds of said pad forms said peak.

5. The pad of claim 4 wherein said continuous peak is formed by a longitudinal fold.

6. The pad of claim 1 wherein said pad has a width of about 2.5 inches.

7. The pad of claim 1 wherein said pad comprises a concave shaped front portion.

8. The pad of claim 1 wherein said pad has an hourglass shape.

9. The pad of claim 1 wherein said rearward peak extends to the area between the buttocks.

10. The pad of claim 1 wherein a higher density absorbent layer is adjacent said backing layer and a lower density absorbent is adjacent said bodyside web.

11. The pad of claim 1 wherein the length of said pad is between about 7 and about 12 inches.

12. The pad of claim 11 wherein the width of said pad is between about 2 and about 4 inches.

13. The pad of claim 1 wherein said peak is formed by an adhesively held tuck.

14. The pad of claim 13 wherein said tuck is between about ⅛ and about ⅜ inch deep.

15. The pad of claim 13 wherein the adhesive bond of said tuck may be partially broken to shape said pad.

16. The pad of claim 2 wherein said peak extends to the rearward end of said pad.

17. The pad of claim 1 wherein said pad is of greater distance across the forward end than at the rear end.

18. The pad of claim 1 wherein said pad is a greater distance transversely across in the rear area than the forward area.

19. The pad of claim 2 wherein said pad is provided with grooves that form a V extending from a beginning point for both lines near the front of the pad and extending on each side of said peak.

20. The pad of claim 19 wherein said pad is folded with a fold along the line of the peak such that the sides of said backing sheet are in contact with each other and folds on said grooves such that the bodyside areas outside of said grooves are in contact with each other.

21. A pad for absorption of human exudate comprising an impermeable outer cover, a permeable body side web and an absorbent therebetween, said pad having a length greater than about 7 inches comprising a front portion adapted to form a flattened or concave portion for positioning exterior of the clitoris and pubic mons and a rearward portion adapted to yield a raised peak forming the pad into an inverted V shape for positioning in alignment with the creases of the perineum and buttocks.

* * * * *